US00PP36058P2

(12) United States Plant Patent
Howell

(10) Patent No.: US PP36,058 P2
(45) Date of Patent: Aug. 6, 2024

(54) APPLE TREE NAMED 'HOWELL TC11'

(50) Latin Name: *Malus domestica*
Varietal Denomination: Howell TC11

(71) Applicant: William Edward Howell, Prosser, WA (US)

(72) Inventor: William Edward Howell, Prosser, WA (US)

( * ) Notice: Subject to any disclaimer, the term of this patent is extended or adjusted under 35 U.S.C. 154(b) by 0 days.

(21) Appl. No.: 18/386,990

(22) Filed: Nov. 3, 2023

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

A new and distinct apple tree named 'Howell TC11' characterized by its fruit, which has an attractive red overcolor and distinctive red, red-purple and yellow-white flesh.

4 Drawing Sheets

Latin name: *Malus domestica.*
Variety denomination: 'Howell TC11'.

BACKGROUND OF THE VARIETY

The new apple tree 'Howell TC11' was created in the course of a planned breeding program carried out at Prosser, Washington. 'Howell TC11' originated from a controlled cross of 'Honeycrisp' (pollen parent, U.S. Plant Pat. No. 7,197) and 'Arlie Red Flesh' (seed parent, not patented). The cross was carried out in 2001 at Prosser, Washington. 'Howell TC11' was selected from a population of seedlings derived from the parents for further observation, and was first asexually propagated by bud grafting in 2015 in Prosser, Washington. 'Howell TC11' trees have been observed over a number of asexually propagated generations, and have been found to remain true to type.

'Howell TC11' was selected for its attractive, red-fleshed later-maturing fruit. It is distinguished from its parents by the characteristics set forth in Table 1.

TABLE 1

Comparison of 'Howell TC11' to 'Honeycrisp' and 'Arlie Red Flesh'

| Characteristic | 'Arlie Red Flesh' | 'Honeycrisp' | 'Howell TC11' |
|---|---|---|---|
| Fruit size | Small to medium, 60 mm to 70 mm | Medium to large, 70 mm to 90 mm | Medium, 70 mm to 80 mm |
| Fruit shape | Conic | Globose-oblate | Globose-conic |
| Flesh color | Red | Yellow-white | Red purple and yellow-white |
| Flavor | Sweet-tart | Sweet, sub-acid | Sweet-tart with berry flavor notes |
| Flower color | Lavender | White | White with red-purple |

'Howell TC11' is distinguished from red-fleshed apple varieties 'Howell TC2' (U.S. Plant Pat. No. 28,545) and 'Pink Pearl' (U.S. Plant Pat. No. 723) by the characteristics set forth in Table 2.

TABLE 2

Comparison of 'Howell TC11' to 'Howell TC2' and 'Pink Pearl'

| Characteristic | 'Howell TC2' | 'Pink Pearl' | 'Howell TC11' |
|---|---|---|---|
| Fruit shape | Globose | Conic | Globose-conic |
| Flesh color | Red and white | Pink | Red-purple and yellow-white |
| Flower color | Pinkish-red | Pink | White with red-purple |
| Harvest maturity | Mid- to late September | Early September | Mid-October |

BRIEF DESCRIPTION OF THE PHOTOGRAPHS

The attached photographs of 5-year-old 'Howell TC11' trees and their flowers and fruit were taken at Wapato, Washington during the 2023growing season. The trees were grown on 'M9' rootstock (not patented).

DETAILED BOTANICAL DESCRIPTION OF THE VARIETY

Figure 1:
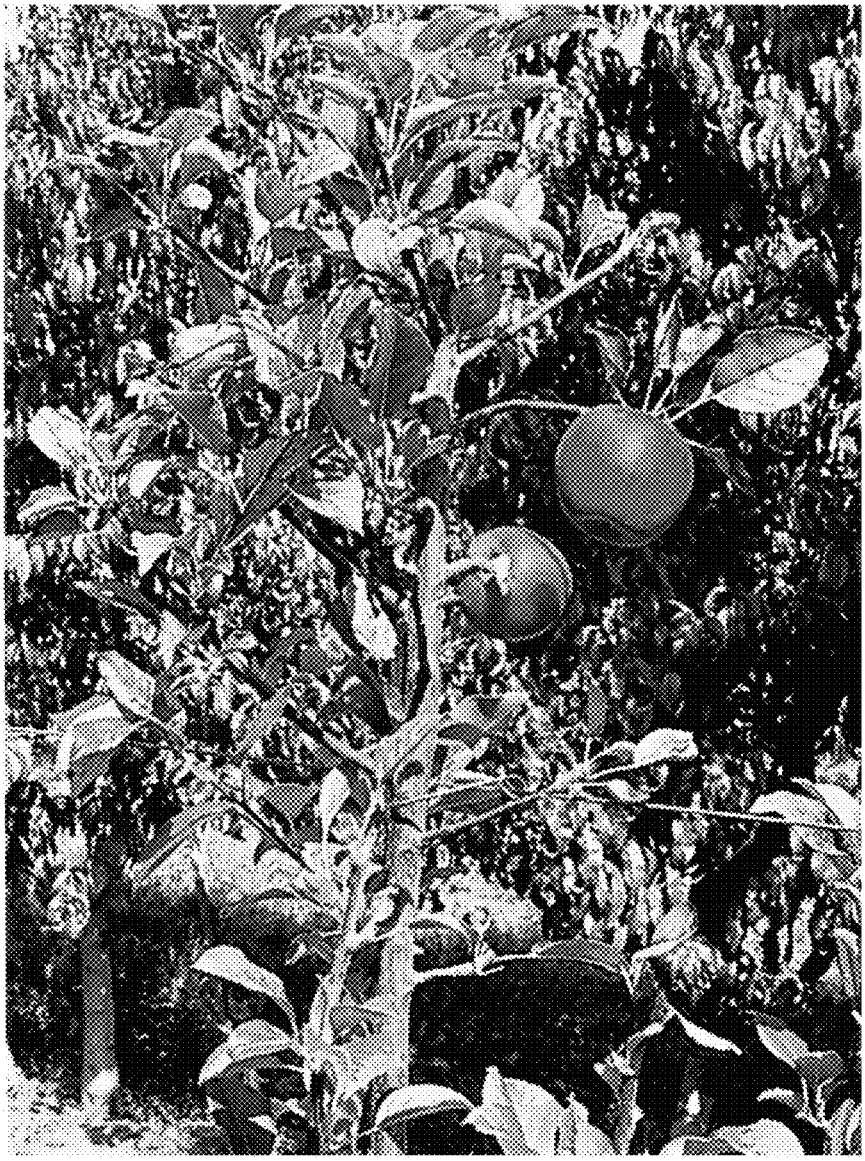
FIG. 1 shows the fruit, branches and leaves on a 'Howell TC11' apple tree.
Figure 2:
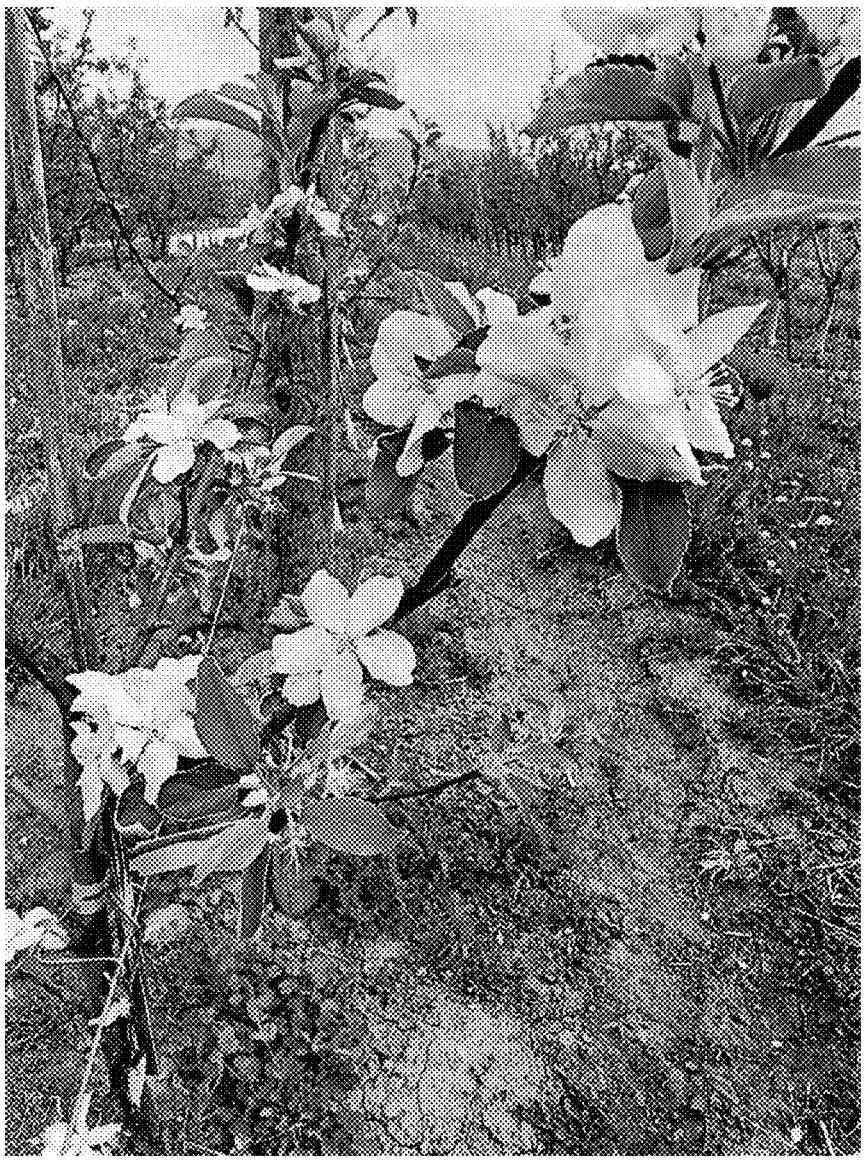
FIG. 2 shows blossoms on a 'Howell TC11' apple tree.

The following detailed botanical description was recorded at Wapato, Washington during the 2023 growing season. The described trees were planted in 2018 on 'M9' rootstock. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. All colors are described with reference to The R.H.S. Colour Chart, 4th ed. (Royal Horticultural Society, 2001).

Tree:
- *Vigor.*—Semi-vigorous.
- *Type.*—Ramified.
- *Habit.*—Spreading.
- *Height.*—3.0 m.
- *Spread.*—75 cm.
- *Trunk diameter* (*at* 30 *cm above the graft*).—3 cm.
- *Bearing.*—On spurs and shoots.
- *Bark texture.*—Rough.
- *Bark color.*—Greyed-orange 166C.
- *Lenticel length.*—6 mm.
- *Lenticel width.*—1 mm.
- *Lenticel shape.*—Elongated.
- *Lenticel color.*—White N155A.
- *Lenticel density.*—12 per 4 $cm^2$.

Branch (fruiting branches located at around 1 m above the graft union):
- *Length.*—53 cm.
- *Diameter.*—8 mm.
- *Crotch angle.*—80°.
- *Bark color.*—Grey-brown N199B.
- *Branch lenticel length.*—1 mm.
- *Branch lenticel width.*—1 mm.
- *Branch lenticel shape.*—Oval.
- *Branch lenticel color.*—White N155D.
- *Branch lenticel density.*—15 per $cm^2$.

One year old shoot:
- *Length.*—23 cm.
- *Diameter.*—3 mm.
- *Color.*—Greyed-orange 165A.
- *Pubescence.*—Present.
- *Internode length.*—4 cm.
- *Shoot lenticel length.*—0.5 mm.
- *Shoot lenticel width.*—0.5 mm.
- *Shoot lenticel shape.*—Oval.
- *Shoot lenticel color.*—White N155D.
- *Shoot lenticel density.*—16 per $cm^2$.

Flower Buds:
- *Stage described.*—Tight.
- *Quantity per spur.*—4 to 5.
- *Bud shape.*—Ovate.
- *Apex shape.*—Acute.
- *Length.*—7.2 mm.
- *Diameter.*—5.0 mm.
- *Color.*—Red 52B.

Flowers:
- *Diameter of fully open flower.*—32 mm.
- *Relative position of petal margins.*—Overlapping.
- *Number per cluster.*—4 to b 5.
- *Date of first bloom.*—Apr. 27, 2023.
- *Date of full bloom.*—May 4, 2023.
- *Pollination requirement.*—Pollenizer required.

Petals:
- *Number per flower.*—5.
- *Petal length.*—17 mm.
- *Petal width.*—10 mm.
- *Petal shape.*—Obovate, obtuse tip; cuneate base; margin entire, ruffled.
- *Petal texture-upper surface.*—Smooth.
- *Color-upper surface.*—White N155B with red-purple 65D near base.
- *Color-lower surface.*—Red-purple 65D.

Pistils:
- *Quantity per flower.*—4.
- *Length.*—0.3 mm.
- *Color.*—Green 143B.

Stigma:
- *Length.*—1 mm.
- *Diameter.*—1 mm.
- *Color* Green.—143B.

Style:
- *Length.*—5.8 mm.
- *Color.*—Yellow 8B.

Ovary:
- *Length.*—3.7 mm.
- *Diameter.*—2.6 mm.
- *Color.*—Green 139C.

Stamens:
- *Quantity.*—14.
- *Length.*—3.7 mm.
- *Anther color.*—Yellow 10B.
- *Pollen.*—Present in moderate amount; yellow 10B.

Pedicel:
- *Length.*—13 mm.
- *Diameter.*—2.2 mm.
- *Color.*—Green 142C.

Sepals:
- *Quantity.*—5.
- *Color.*—Green 142C.
- *Length.*—9 mm.
- *Width.*—4 mm at widest point.
- *Shape.*—Lanceolate.
- *Apex.*—Acuminate.
- *Margin.*—Entire.

Leaves:
- *Shape.*—Oval.
- *Length.*—7.5 cm.
- *Width.*—5 cm.
- *Blade margin.*—Serrate.
- *Apex.*—Acuminate.
- *Base shape.*—Rounded.
- *Color of upper surface.*—Yellow-green 146A.
- *Color of lower surface.*—Yellow-green 146B.
- *Texture of upper surface.*—Smooth.
- *Texture of lower surface.*—Smooth.
- *Attitude in relation to shoot.*—Upward.

Petiole:
- *Length.*—2.5 cm.
- *Diameter.*—2 mm.
- *Color.*—Yellow-green 145C.
- *Stipule quantity.*—2.
- *Stipule shape.*—Elongated.
- *Stipule length.*—5 mm.
- *Stipule width.*—1 mm.
- *Stipule color.*—Yellow-green 146B.

Fruit:
- *Quantity per cluster.*—2 to 3 (after thinning).
- *Diameter.*—7 cm to 8 cm.
- *Height.*—5 cm to 6 cm.
- *Weight.*—200 g.
- *General shape in profile.*—Globose-conic.
- *Position of maximum diameter.*—At equator.
- *Ribbing.*—None.
- *Crowning at calyx end.*—Yes.
- *Aperture of eye.*—Mostly closed.
- *Depth of eye basin.*—0.5 cm.
- *Width of eye basin.*—2.5 cm.

*Bloom of skin.*—Absent.
*Greasiness of skin.*—Present.
*Background color of skin.*—Yellow 1D.
*Overcolor of skin.*—Red 42A.
*Amount of overcolor.*—90%.
*Intensity of overcolor.*—High.
*Pattern of overcolor.*—Solid flush.
*Amount of russet around stalk cavity.*—20%.
*Russet on cheeks.*—Absent.
*Russet around eye basin.*—Absent.
*Length of stalk.*—2.5 cm.
*Diameter of stalk.*—0.3 cm.
*Stalk color.*—Green 135D.
*Depth of stalk cavity.*—1.1 cm.
*Width of stalk cavity.*—1.6 cm.

Figure 3:
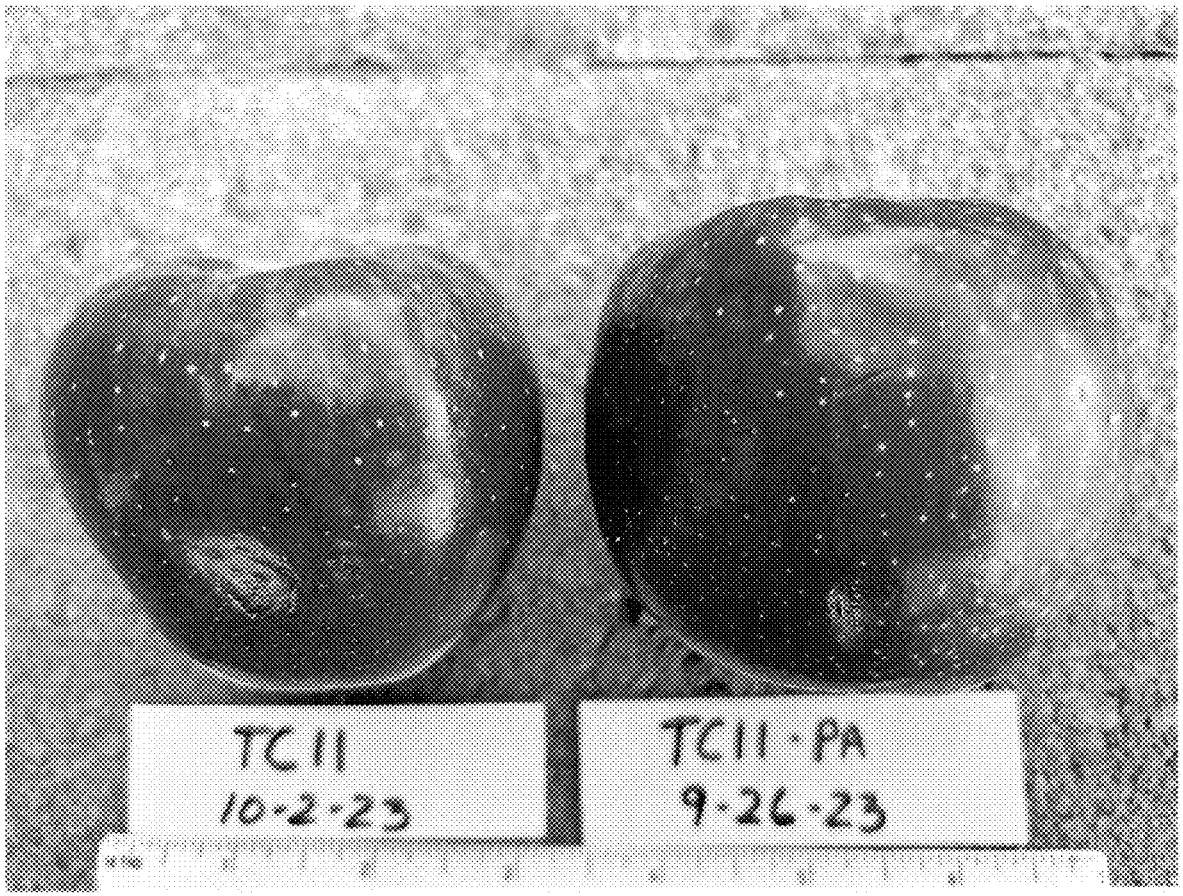
FIG. 3 shows whole fruit from a 'Howell TC11' apple tree.
Figure 4:
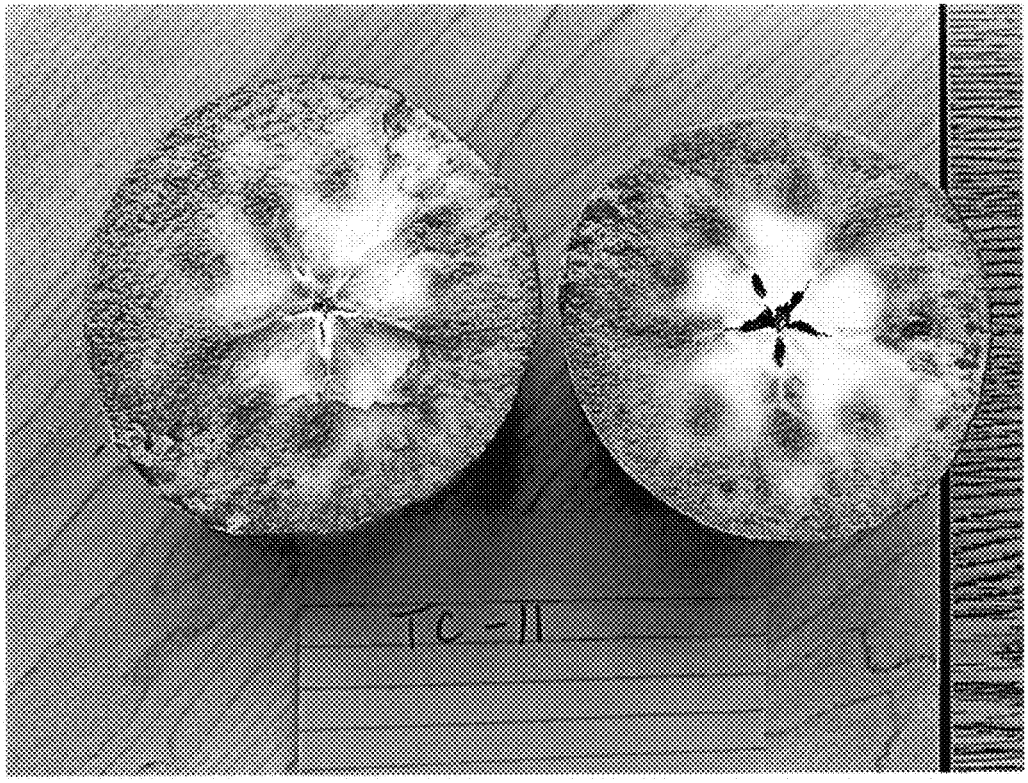
FIG. 4 shows sectioned fruit from a 'Howell TC11' apple tree.

Flesh:

*Color.*—Outer portion red-purple 58B near skin fading to red 58C halfway to center; inner portion yellow-white 155B; see FIG. 3 and FIG. 4.
*Firmness.*—Firm, average pressure 18 PSI.
*Texture.*—Fine, crunchy.
*Aroma.*—Present.
*Juiciness.*—High.
*Flavor.*—Sweet-tart with berry flavor notes.
*Brix.*—11° Brix.
*Eating quality.*—Excellent.

Seeds:

*Quantity per fruit.*—10.
*Shape.*—Ovate.
*Length.*—7 mm.
*Width.*—3 mm.
*Color.*—Greyed-orange 178A.
*Locules.*—10 per fruit; length 15 mm, width 10 mm.

Harvest:

*Time for harvest.*—About Oct. 17, 2023.
Number of picks.—1.
*Disease and pest resistance.*—None noted.
*Market use.*—Fresh.

I claim:

1. A new and distinct apple tree named 'Howell TC11' substantially as described and illustrated herein.

* * * * *